US00PP24759P2

(12) United States Plant Patent

Iredell et al.

(10) Patent No.: US PP24,759 P2

(45) Date of Patent: Aug. 12, 2014

(54) ***BOUGAINVILLEA* PLANT NAMED 'IREBABS6'**

(50) Latin Name: *Bougainvillea×spectro-glabra*
Varietal Denomination: IREBABS6

(71) Applicants: Janet Willa Iredell, Brisbane (AU); Peter Dawborn Iredell, Brisbane (AU)

(72) Inventors: Janet Willa Iredell, Brisbane (AU); Peter Dawborn Iredell, Brisbane (AU)

( * ) Notice: Subject to any disclaimer, the term of this patent is extended or adjusted under 35 U.S.C. 154(b) by 0 days.

(21) Appl. No.: 13/998,994

(22) Filed: Dec. 31, 2013

(51) Int. Cl.
*A01H 5/00* (2006.01)

(52) U.S. Cl.
USPC ..... Plt./256

(58) Field of Classification Search
CPC ..... A01H 5/02
USPC ..... Plt./256
See application file for complete search history.

*Primary Examiner* — June Hwu

(74) *Attorney, Agent, or Firm* — Barbara Campbell; Cochran Freund & Young LLC

(57) ABSTRACT

A *Bougainvillea* plant particularly distinguished by a rounded, low growing, and spreading shrub, prolific flowering, purple-violet bracts, and variegated foliage, is disclosed.

2 Drawing Sheets

Genus and species: *Bougainvillea×spectro-glabra.*
Variety denomination: 'IREBABS6'.

BACKGROUND OF THE NEW PLANT

The present invention comprises a new and distinct variety of *Bougainvillea*, botanically known as *Bougainvillea×spectro-glabra*, and hereinafter referred to by the variety name 'IREBABS6'. The new variety originated from a branch mutation of the *Bougainvillea* parent 'Nonya' (unpatented) in October 1997.

The new plant was first asexually propagated May 1998 in Brisbane, Australia and has been asexually reproduced by cuttings for numerous generations in Brisbane, Australia. The present invention has been found to retain its distinctive characteristics through successive asexual propagations by cuttings.

'IREBABS6' has not been made publicly available or sold more than one year prior to the filing of this application.

SUMMARY

The following are the most outstanding and distinguishing characteristics of the new variety when grown under normal horticultural practices in Brisbane, Australia.

1. A rounded, low growing, and spreading shrub; and
2. Having prolific flowering, purple-violet bracts and variegated foliage.

DESCRIPTION OF THE PHOTOGRAPHS

This new *Bougainvillea* plant is illustrated by the accompanying photographs which show the foliage and colored bracts of the plant. The colors are as true as can be reasonably obtained by conventional photographic procedures of plants grown outdoors in Brisbane, Australia.

DESCRIPTION OF THE NEW VARIETY

Figure 1:
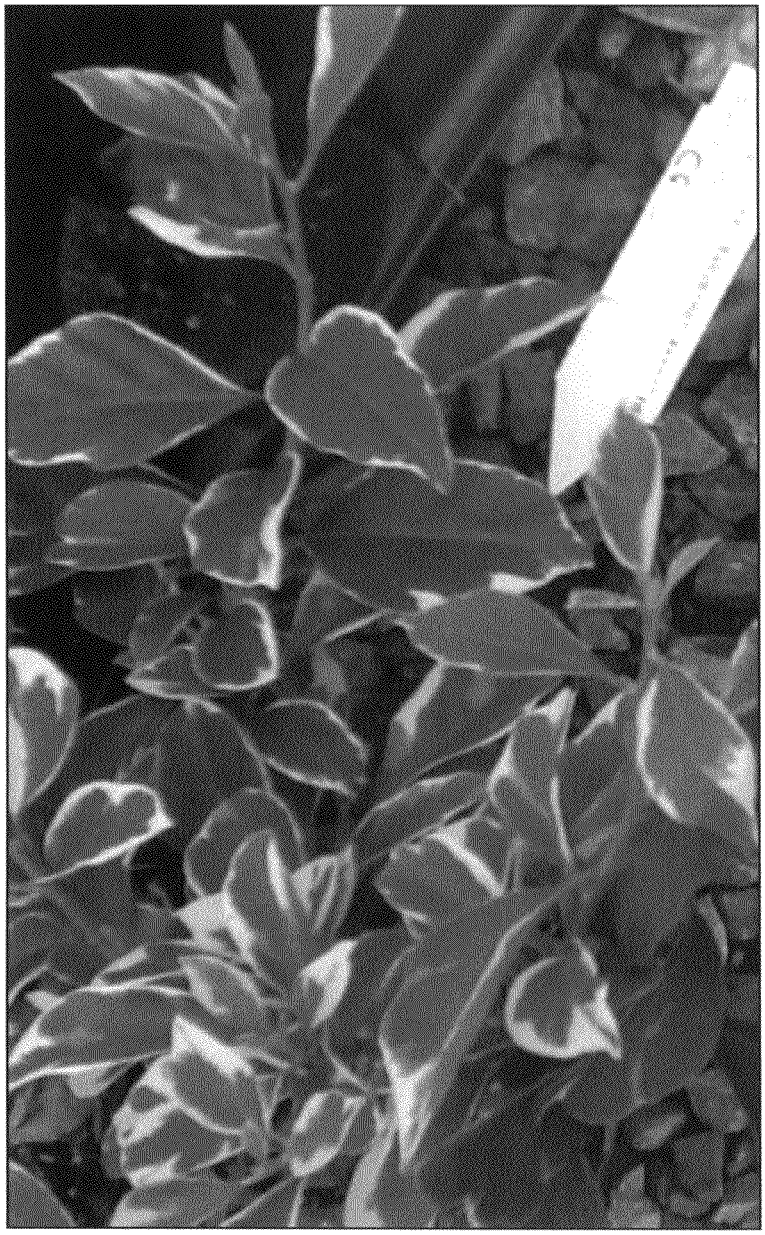
FIG. 1 shows a close-up of the variegated foliage a plant approximately less than one-year-old.
Figure 2:
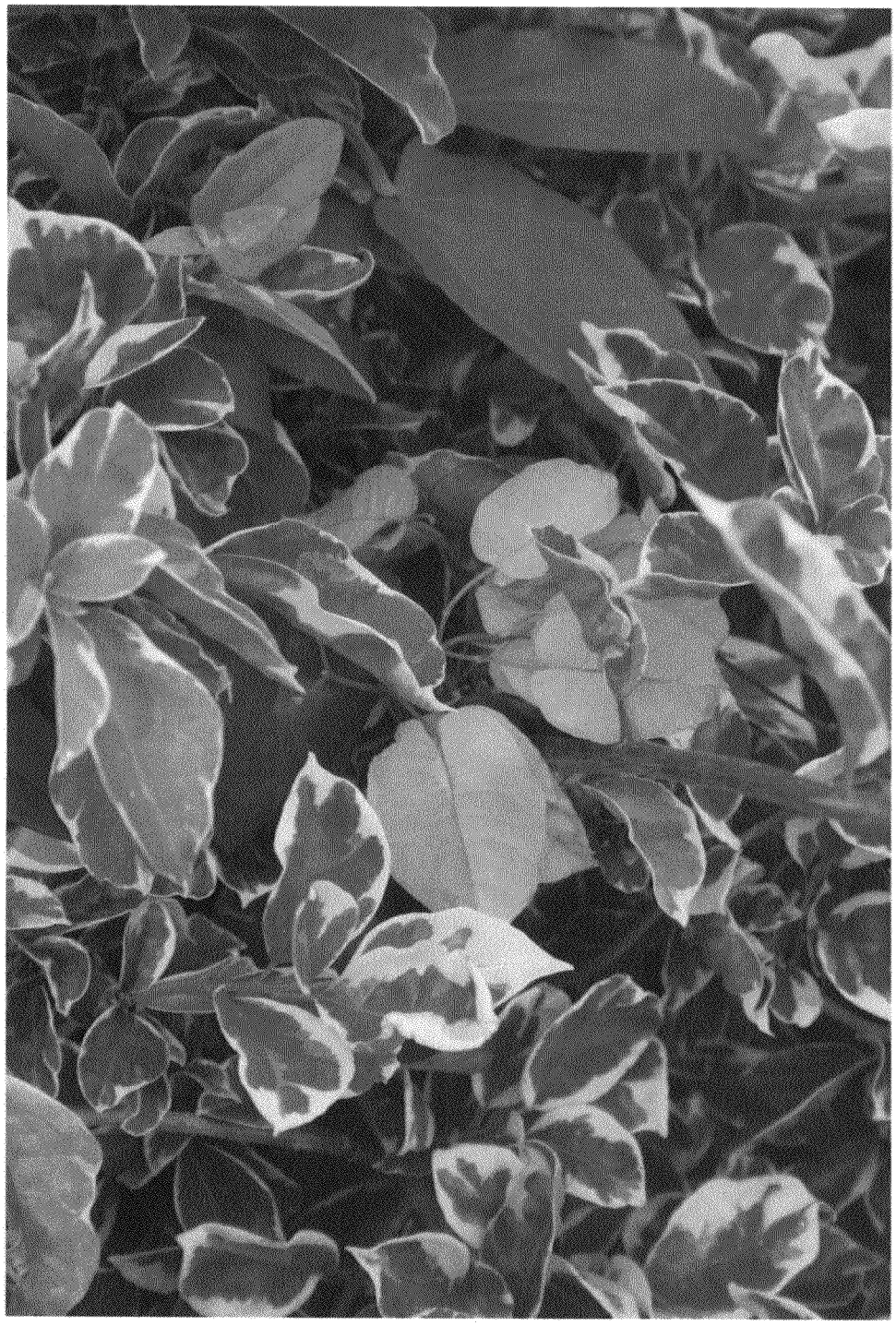
FIG. 2 shows a close-up of the variegated foliage and bracts of a plant approximately six-years-old.

The following detailed descriptions set forth the distinctive characteristics of 'IREBABS6'. The data which defines these characteristics were collected from asexual reproductions carried out in Brisbane, Australia. The plant history was taken in May 2013 on five-year-old plants grown outdoors in Brisbane, Australia. Color references were taken under natural light and are to The R.H.S. Colour Chart of The Royal Horticultural Society of London (R.H.S. 2001).

Classification:
- *Family.*—Nyctaginaceae.
- *Botanical name.*—*Bougainvillea×spectro-glabra.*
- *Common name.*—*Bougainvillea.*
- *Denomination.*—'IREBABS6'.

Plant:
- *Type.*—Shrub and perennial (in warmer climates).
- *Form.*—Rounded.
- *Habit.*—Low growing and spreading.
- *Appropriate containers.*—Commercial pots of all sizes.
- *Time to produce a finished flowering plant.*—12 weeks from a cutting.
- *Growth rate.*—Moderate.
- *Vigor.*—Strong.
- *Height (measured from the top of the soil).*—60.0 cm to 100.0 cm.
- *Width (horizontal plant diameter).*—100.0 cm.
- *Pinching required.*—Yes, at liner stage.
- *Propagation type.*—Cuttings.

Lateral branches:
- *Branching habit.*—Horizontal.
- *Length.*—About 60.0 cm.
- *Diameter.*—1.5 cm to 2.0 cm.
- *Internode length.*—4.0 mm to 15.0 mm.
- *Shape (cross-section).*—Round.
- *Aspect.*—Horizontal.
- *Strength.*—Strong.
- *Color.*—RHS 199B.

*Pubescence*.—Absent.

*Thorns*.—Size: 0.6 cm in length; 0.2 cm in width (at the base where the thorns meet the branch). Quantity: Not at every leaf node but at approximately 90% of the leaf nodes. Color: RHS 199B.

Foliage:

*Quantity of leaves per lateral branch*.—Over 60.

*Arrangement*.—Alternate, single.

*Durability of foliage to stresses*.—Strong.

*Length*.—2.5 cm to 2.55 cm.

*Width*.—1.2 cm to 1.4 cm.

*Shape*.—Broadly ovate.

*Apex*.—Acute.

*Base*.—Cordate.

*Margin*.—Entire.

*Color, immature*.—Upper surface: RHS 139A. Lower surface: RHS N138B.

*Color, mature*.—Upper surface: RHS 147A, RHS 10A for margins. Lower surface: RHS 138B, RHS 10B for margins.

*Texture*.—Both upper and lower surfaces: Glabrous, smooth; pubescence is absent.

*Venation type*.—Pinnate.

*Venation color*.—Upper surface: RHS 139A. Lower surface: RHS N138A.

*Petiole*.—Color: RHS N138A. Length: 0.5 cm. Diameter: 0.25 cm.

Inflorescence: Height: 4.0 cm to 5.0 cm. Width: 5.0 cm.

*Bud*.—Color: Purple-violet. Height: 0.9 cm to 1.5 cm. Diameter: 0.5 cm to 1.5 cm.

*Flower*.—Type and habit: Single flowers arranged in axillary panicles; flowers are upright and self-cleaning. Fragrance: Absent. Aspect: Upright. Flowering season: Profuse flowering; flowers in autumn, the spring and regions with mild winters. Diameter: 1.5 cm to 2.0 cm. Quantity per lateral stem: Over 80. Quantity of flowers per inflorescence: 8 to 10. Flower tube (perianth): Width: 0.35 cm to 0.40 cm. Length: 2.0 cm. Color: RHS 155B. Quantity per flower: 3; composed of 5 fused petals. Bracts: Quantity per flower: 3. Length: 1.5 cm to 2.5 cm. Width: 1.5 cm to 2.0 cm. Apex: Acute. Margin: Entire. Color, when opening: Upper surface: RHS N81B. Lower surface: RHS N81C. Color, when open: Upper surface: RHS N81B. Lower surface: RHS N81C. Peduncle: Length: 0.5 cm to 0.8 cm. Diameter: 0.1 cm. Angle: 30°. Strength: Strong. Color: RHS 138A. Pedicel: Length: 0.2 cm to 0.3 cm. Diameter: 0.1 cm. Angle: 25°. Strength: Moderate. Color: RHS 138A.

Fruit and seed set: None observed.

Disease and insect resistance: No specific disease or insect resistance observed.

Reproductive organs: None observed.

COMPARISON WITH PARENTAL AND COMMERCIAL VARIETY

'IREBABS6' differs from the mutation parent *Bougainvillea* parent 'Nonya' in that 'IREBABS6' has variegate foliage, while 'Nonya' does not have variegated foliage. Additionally, 'IREBABS6' has a lower growing habit than 'Nonya'.

'IREBABS6' differs from the commercial comparison 'Beesnees' (U.S. Plant Pat. No. 16,946) in that 'IREBABS6' has 3 unfused bracts per flower, while 'Beesnees' has 5 fused bracts per flower.

We claim:

1. A new and distinct variety of *Bougainvillea* plant as shown and described herein.

* * * * *